(12) United States Patent
Hara et al.

(10) Patent No.: US 11,715,567 B2
(45) Date of Patent: Aug. 1, 2023

(54) STORAGE MEDIUM, INFORMATION PROCESSING APPARATUS, INFORMATION PROCESSING SYSTEM, AND INFORMATION PROCESSING METHOD

(71) Applicant: TOYOTA JIDOSHA KABUSHIKI KAISHA, Toyota (JP)

(72) Inventors: Yusuke Hara, Musashino (JP); Shuhei Aketa, Koto-ku (JP); Toru Yanagida, Nagoya (JP); Shin Sakurada, Toyota (JP); Tae Sugimura, Miyoshi (JP); Yasutaka Ujihara, Meguro-ku (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 337 days.

(21) Appl. No.: 17/079,018

(22) Filed: Oct. 23, 2020

(65) Prior Publication Data

US 2021/0151197 A1 May 20, 2021

(30) Foreign Application Priority Data

Nov. 14, 2019 (JP) .................................. 2019-206442

(51) Int. Cl.
*G16H 50/70* (2018.01)
*G16H 40/67* (2018.01)
(Continued)

(52) U.S. Cl.
CPC .............. *G16H 50/70* (2018.01); *A61B 5/117* (2013.01); *A61B 5/6893* (2013.01); *G06Q 50/30* (2013.01); *G16H 10/60* (2018.01); *G16H 15/00* (2018.01); *G16H 40/67* (2018.01); *G16H 50/30* (2018.01); *H04L 63/0861* (2013.01); *G05D 1/0088* (2013.01); *G16H 50/20* (2018.01)

(58) Field of Classification Search
CPC combination set(s) only.
See application file for complete search history.

(56) References Cited

U.S. PATENT DOCUMENTS 9,846,716 B1 * 12/2017 Scott .................... G06F 16/2365
2003/0038047 A1 * 2/2003 Sleva ...................... A61B 50/31
206/370

(Continued)

FOREIGN PATENT DOCUMENTS

JP 2006-302206 A 11/2006
JP 2009-217386 A 9/2009
(Continued)

OTHER PUBLICATIONS

C. Wahane, Varsha; Ingole, P V., Interactive Mobile Health Monitoring System, International Journal of Advanced Computer Science and Applications , 8.4 Science and Information (SAI) Organization Limited. (2017) (Year: 2017).*

*Primary Examiner* — Amber A Misiaszek
(74) *Attorney, Agent, or Firm* — Oliff PLC (57) ABSTRACT

A storage medium stores a program. The program causes a first terminal apparatus to execute processing including: obtaining biological information on a subject from a first sensor provided in a mobile object, obtaining identification information for the subject, obtaining a detection time, and sending the biological information in association with the identification information for the subject and the detection time to an information processing apparatus.

11 Claims, 6 Drawing Sheets

(51) Int. Cl.
*G16H 15/00* (2018.01)
*G16H 10/60* (2018.01)
*G16H 50/30* (2018.01)
*H04L 9/40* (2022.01)
*A61B 5/00* (2006.01)
*A61B 5/117* (2016.01)
*G06Q 50/30* (2012.01)
*G05D 1/00* (2006.01)
*G16H 50/20* (2018.01)

(56) References Cited

U.S. PATENT DOCUMENTS

| | | | |
|---|---|---|---|
| 2012/0236053 A1* | 9/2012 | Tamura | B41J 2/0458 |
| | | | 347/10 |
| 2015/0193588 A1 | 7/2015 | Nemoto et al. | |
| 2017/0011223 A1* | 1/2017 | Dang | G06F 21/606 |
| 2017/0132376 A1* | 5/2017 | Bangera | G16H 40/20 |
| 2021/0236053 A1* | 8/2021 | Narayan | A61B 5/363 |

FOREIGN PATENT DOCUMENTS

| | | |
|---|---|---|
| JP | 2011-227547 A | 11/2011 |
| WO | 2015/050174 A1 | 4/2015 |

\* cited by examiner

STORAGE MEDIUM, INFORMATION PROCESSING APPARATUS, INFORMATION PROCESSING SYSTEM, AND INFORMATION PROCESSING METHOD

CROSS-REFERENCE TO RELATED APPLICATION

This application claims priority to JP 2019-206442 filed on Nov. 14, 2019, the entire disclosure of which is incorporated herein by reference.

TECHNICAL FIELD

The present disclosure relates to a storage medium, an information processing apparatus, an information processing system, and an information processing method.

BACKGROUND

Biological information obtained at multiple time points for individuals in a group is beneficial for understanding the health conditions and trends of diseases for the group, and the like. The biological information of individuals has been collected, for example, in medical facilities, or otherwise in the homes of individuals by using user terminals in the possession of individuals who desire to receive medical services (refer to JP 2011-227547 A (PTL 1)).

CITATION LIST

Patent Literature

PTL 1: JP 2011-227547 A

SUMMARY

The biological information collected at medical facilities is, however, usually biological information on sick or injured patients, and thus this kind of information has difficulty in representing biological information on a group that is not limited to sick or injured patients, such as a population in a particular area. Biological information on people including healthy individuals can be collected by mass screening or the like. Yet, since it is difficult to frequently conduct mass screening, biological information on individuals at multiple time points cannot be easily collected.

The present disclosure has been made in view of the above circumstances, and an object thereof is to provide a storage medium, an information processing apparatus, an information processing system, and an information processing method that enable collection of biological information on a group that is not limited to sick or injured patients at multiple time points.

A non-transitory computer-readable storage medium according to an embodiment of the present disclosure stores a program. The program causes a computer to execute processing including: obtaining biological information on a subject from a first sensor provided in a mobile object, obtaining identification information for the subject, obtaining a detection time indicating when the biological information is detected, and sending the biological information in association with the identification information for the subject and the detection time to an information processing apparatus.

An information processing apparatus according to an embodiment of the present disclosure includes a controller configured to, when biological information on a subject is received in association with identification information for the subject and a detection time indicating when the biological information is detected, retrieve a biological information record for the subject associated with the identification information from a biological information database and send response information based on the biological information on the subject and the biological information record.

An information processing system according to an embodiment of the present disclosure includes an information processing apparatus and a terminal apparatus. The information processing apparatus includes a controller configured to, when biological information on a subject is received in association with identification information for the subject and a detection time indicating when the biological information is detected, retrieve a biological information record for the subject associated with the identification information from a biological information database and send response information based on the biological information on the subject and the biological information record. The terminal apparatus is configured to obtain biological information on a subject from a first sensor provided in a mobile object, obtain identification information for the subject, obtain a detection time indicating when the biological information is detected, and send the biological information in association with the identification information for the subject and the detection time to the information processing apparatus.

An information processing method according to an embodiment of the present disclosure is implemented by a computer, in which the computer obtains biological information on a subject from a first sensor provided in a mobile object, obtains identification information for the subject, obtains a detection time indicating when the biological information is detected, and sends the biological information in association with the identification information for the subject and the detection time to an information processing apparatus.

The storage medium, the information processing apparatus, the information processing system, and the information processing method according to an embodiment of the present disclosure enable collection of biological information on a group that is not limited to sick or injured patients at multiple time points.

DETAILED DESCRIPTION

Hereinafter, an embodiment of the present disclosure will be described with reference to the drawings.

Figure 1:
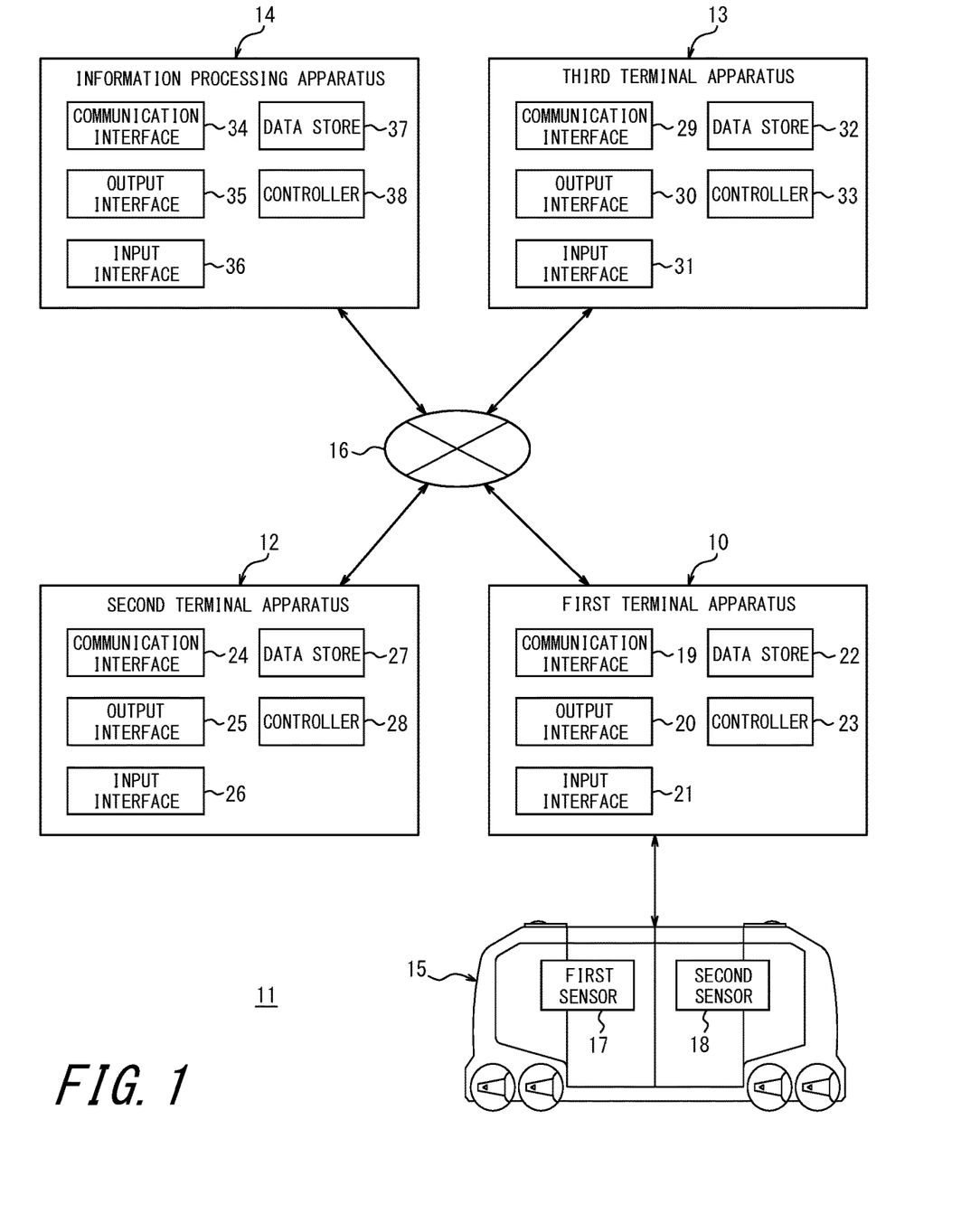
FIG. 1 is a configuration diagram illustrating an overall configuration of an information processing system including a first terminal apparatus that runs a program stored in a storage medium according to an embodiment of the present disclosure.

An information processing system 11 including a first terminal apparatus (a computer) 10 configured to run a program stored in a storage medium according to an embodiment of the present disclosure will be outlined with reference to FIG. 1. The information processing system 11 includes the first terminal apparatus 10, a second terminal apparatus 12, a third terminal apparatus 13, and an information processing apparatus 14.

The first terminal apparatus 10, the second terminal apparatus 12, and the third terminal apparatus 13 are each, for example, a portable terminal apparatus, such as a smartphone, or a general electronic device, such as a personal computer (PC), but the first terminal apparatus 10, the second terminal apparatus 12, and the third terminal apparatus 13 are not limited to these examples and each may be an electronic device dedicated the information processing system 11. The first terminal apparatus 10 is installed and used in, for example, a mobile object 15 such as a vehicle to be boarded by a subject. The second terminal apparatus 12 is carried by, for example, an individual who boards the mobile object 15. The third terminal apparatus 13 is installed at, for example, a medical facility. The information processing apparatus 14 includes one server apparatus or a plurality of server apparatuses that are capable of communicating with each other. While FIG. 1 illustrates one first terminal apparatus 10, one second terminal apparatus 12, and one third terminal apparatus 13 for ease of description, the information processing system 11 only needs to include at least one first terminal apparatus 10, at least one second terminal apparatus 12, and at least one third terminal apparatus 13.

The first terminal apparatus 10, the second terminal apparatus 12, the third terminal apparatus 13, and the information processing apparatus 14 are each communicably connected to a network 16 which includes, for example, a mobile communication network and the Internet. At least part of the information processing system 11 is used for providing a mobility service (MaaS: Mobility-as-a-Service). Service providers can provide mobility services such as ridesharing services, mobile hotels, and mobile retail shops by using the first terminal apparatus 10 and the mobile object 15.

The outline of the present embodiment will be further explained. The first terminal apparatus 10 obtains biological information on a subject such as a crew member or a passenger of the mobile object 15 using the first terminal apparatus 10 together with identification information for the subject, associates the information with each other, and sends it to the information processing apparatus 14. When the information processing apparatus 14 receives the biological information, the information processing apparatus 14 updates a particular biological information record for the subject associated with the received identification information for the subject in a biological information database. Additionally, the information processing apparatus 14 generates response information based on the updated record, that is, the biological information record for the subject in the biological information database and the received biological information. The information processing apparatus 14 sends the response information to at least one of the first terminal apparatus 10 and the second terminal apparatus 12. At least one of the first terminal apparatus 10 and the second terminal apparatus 12, having received the response information, notifies the subject of the health condition of the subject, based on the response information.

Next, each component of the information processing system 11 will be described in detail.

The first terminal apparatus 10 is, as described above, installed in the mobile object 15 and used in the mobile object 15 for, for example, automated driving of the mobile object 15. For example, the mobile object 15 is, but not limited to, an autonomous vehicle that can perform automated driving or adaptive cruise control, but is not limited to this, and the mobile object 15 may be any mobile object in which the first terminal apparatus 10 can be installed and to which a subject can boards, such as a vehicle, a ship, or an airplane.

The first terminal apparatus 10 may automatically generate control information by using automatic driving control software, and send the control information to the mobile object 15. The mobile object 15 may perform vehicle control based on the received control information. For example, the vehicle control may be, but is not limited to, automated driving control. At least part of an application programming interface (API), in which specifications of control information are defined, is disclosed to service providers. Service providers can freely develop automatic driving control software of the first terminal apparatus 10 by programming using the disclosed API. Thus, the service providers can provide any mobility service by installing a facility according to a purpose in an interior space of the vehicle cabin of the mobile object 15 and developing automatic driving control software by programming with the use of an API according to the purpose.

A first sensor 17 and a second sensor 18 are provided in the mobile object 15. The first terminal apparatus 10 is attached to the mobile object 15 in a fixed or a detachable manner.

The first sensor 17 includes a sensor configured to detect fluctuating biological information on a subject. The sensor configured to detect the biological information is provided at a position suitable for detection of the biological information in the mobile object 15. The sensor configured to detect the biological information is provided on, for example, a handrail or a steering wheel of the mobile object 15. The sensor configured to detect the biological information includes, for example, a body fat sensor for measuring the body fat percentage, an optical sphygmograph sensor for detecting the pulse and the condition of peripheral blood vessels, a pulse oximeter for measuring the blood oxygen level, an electrocardiograph for detecting the electrical condition of the heart, a temperature sensor for measuring body temperature, and an ultrasonic sensor for detecting internal body conditions. The sensor configured to detect the biological information of the subject may include, for example, a seat sensor that is provided in a seat of the mobile object 15 and a base plate in front of the seat and that is used for measuring weight. The first sensor 17 can communicate with the first terminal apparatus 10 through an in-vehicle network of the mobile object 15, such as a controller area network (CAN), or a dedicated line in the mobile object 15.

The second sensor 18 includes a sensor configured to detect biometric authentication information unique and constant for a subject. The sensor configured to detect the biometric authentication information is provided at a position suitable for detection of the biometric authentication information in the mobile object 15. The sensor configured to detect the biometric authentication information is provided, for example, on the handrail or the steering wheel of the mobile object 15 and in front of a subject, and includes, for example, a fingerprint sensor for detecting a fingerprint, a venous sensor for detecting the venous pattern of a finger, an iris sensor for detecting the iris, a camera for imaging the face, a microphone for detecting the voice, and a retina sensor for detecting the retina. The second sensor 18 can communicate with the first terminal apparatus 10 through an in-vehicle network of the mobile object 15, such as a CAN, or a dedicated line in the mobile object 15.

The first terminal apparatus 10 includes a communication interface 19, an output interface 20, an input interface 21, a data store 22, and a controller 23.

The communication interface 19 includes a communication module that establishes communication through an in-vehicle network of the mobile object 15, such as a CAN, or a dedicated line in the mobile object 15. The communication interface 19 includes a communication module that establishes connection with the network 16. For example, the communication interface may include a communication module compliant with mobile communication standards such as the fourth generation (4G) and the fifth generation (5G) standards. For example, the communication interface 19 may include a communication module compliant with a short-distance wireless communication standard such as Bluetooth® (Bluetooth is a registered trademark in Japan, other countries, or both).

In the present embodiment, the first terminal apparatus 10 is connected to installed devices, such as a control device and a location information acquisition device of the mobile object 15, via the communication interface 19, and communicates information. The first terminal apparatus 10 is also connected to the network 16 via the communication interface 19, or the communication interface 19 and a communication device of the mobile object 15, and transmits and receives various kinds of information through the network 16. Additionally, the first terminal apparatus 10 may be connected to the second terminal apparatus 12 via the communication interface 19 through short-distance wireless communication and communicate various kinds of information. When the communication interface 19 sends information through the network 16, the communication interface 19 may add identification information for the first terminal apparatus 10 to the information. The identification information for the first terminal apparatus 10 is information that can be used to uniquely identify the first terminal apparatus 10 in the information processing system 11.

The output interface 20 includes at least one interface that outputs information to notify a user. For example, the output interface 20 may be, but is not limited to, a display that outputs information as images or a speaker that outputs information as sound.

The input interface 21 includes at least one interface that detects user inputs. The input interface 21 includes, for example, physical keys, capacitive keys, and a touch screen provided in combination with a display of the output interface 20.

The data store 22 may be, but is not limited to, a semiconductor memory, a magnetic memory, an optical memory, or the like. The data store 22 may function as, for example, a primary storage unit, an auxiliary storage unit, or a cache memory. The data store 22 stores any information that is used for operation of the first terminal apparatus 10. The data store 22 may store, for example, a system program and an application program. The information stored in the data store 22 may be updated by using, for example, information received from the network 16 via the communication interface 19.

The controller 23 includes at least one processor. In the present embodiment, a "processor" may be, but is not limited to, a general processor or a processor dedicated to a particular processing operation. The dedicated processor may include an application-specific integrated circuit (ASIC). The controller 23 may include a programmable logic device (PLD). The PLD may include a field-programmable gate array (FPGA). The controller 23 controls the entire operation of the first terminal apparatus 10.

When the input interface 21 detects a user input for requesting detection of biological information, the controller 23 controls the first sensor 17 to detect biological information on a subject. Additionally, the controller 23 obtains a detection time at which the biological information is detected. It should be noted that, as used herein, "obtain" denotes obtaining information on a target such as a detection time. The detection time may be obtained, for example, such that the detection time is received via the communication interface 19 or a timer provided for the first terminal apparatus 10 measures the detection time. The detection time can be any point in time in the period from the start to the end of detection.

Furthermore, when the input interface 21 detects a user input for requesting detection of biological information, the controller 23 controls the communication interface 19 to obtain identification information for the subject. The identification information for the subject is, for example, information that can be used to uniquely identify a particular subject in the information processing system 11. The identification information for the subject includes, for example, mechanical combinations of symbols such as characters and numerals and biometric authentication information for identifying a subject, such as the fingerprint, the venous pattern, the iris, the face, the voiceprint, and the retina. For example, in a case in which short-distance wireless communication can be established via the communication interface 19 with respect to the second terminal apparatus 12 carried by the subject, the controller 23 obtains identification information, such as a combination of symbols, by receiving the identification information from the second terminal apparatus 12. Alternatively, for example, the controller 23 obtains biometric authentication information on a subject by controlling the second sensor 18 via the communication interface 19.

The controller 23 controls the communication interface 19 to send to the information processing apparatus 14 the detected biological information in association with the obtained identification information for the subject and a detection time at which the biological information is detected. The controller 23 may send, as the identification information for the subject, both biometric authentication information and identification information received from the second terminal apparatus 12 in association with the biological information.

When response information is received from the information processing apparatus 14 in response to the sent biological information, the controller 23 notifies the subject of the health condition of the subject, based on the response information. The health condition of the subject includes, for example, information which makes the subject aware of their health condition, such as information about the possibility of developing a disease, such as diabetes, heart disease, or a stroke, information describing a health condition, and suggestions regarding health such as a suggestion about lifestyle, a suggestion regarding a visit to a medical facility, and a suggestion regarding testing.

The response information may be, for example, a health condition of the subject determined by the information processing apparatus 14 based on the biological information record for the subject as described later. Alternatively, the response information may be, for example, a biological information record for the subject sent by the information processing apparatus 14 as described later. Alternatively, the response information may be information for retrieving a health condition of a subject determined and stored by the information processing apparatus 14 based on the biological information record for the subject as described later. The information for retrieving the health condition of the subject includes, for example, information used by the second terminal apparatus 12 to access the information processing apparatus 14 through the network 16 and identifying a health condition of a particular subject in the information processing apparatus 14.

In a case in which the response information is a biological information record for a subject, the controller 23 determines the health condition of the subject based on the record. The determination criteria for determining health condition based on the records may be received via the communication interface 19 or previously received and stored in the data store 22.

The controller 23 presents the health condition of the subject by, for example, outputting the health condition of the subject by using the output interface 20. Alternatively, for example, the controller 23 controls the communication interface 19 to send the health condition of the subject to the second terminal apparatus 12, so that the health condition of the subject is presented by using the second terminal apparatus 12 as described later. It should be noted that, as used herein, "send" denotes sending information on a target such as a health condition. Alternatively, the controller 23 controls the communication interface 19 to send information for retrieving a health condition of a subject determined and stored by the information processing apparatus 14 based on a biological information record for the subject, so that the health condition of the subject is presented by using the second terminal apparatus 12 as described later.

The second terminal apparatus 12 includes a communication interface 24, an output interface 25, an input interface 26, a data store 27, and a controller 28.

The communication interface 24 may include a communication module that establishes a connection with the network 16. For example, the communication interface 24 may include a communication module compliant with a short-distance wireless communication standard such as Bluetooth®. In the present embodiment, the second terminal apparatus 12 is connected to the network 16 via the communication interface 24 and communicates information. Additionally, the second terminal apparatus 12 may be connected to the first terminal apparatus 10 via the communication interface 24 through short-distance wireless communication and communicate various kinds of information. When the communication interface 24 sends information through the network 16, the communication interface 24 may add identification information for the second terminal apparatus 12 to the information. The identification information for the second terminal apparatus 12 is information that can be used to uniquely identify the second terminal apparatus 12 in the information processing system 11.

The specific configuration and the functions of the output interface 25 are similar to the specific configuration and the functions of the output interface 20 of the first terminal apparatus 10. The specific configuration and the functions of the input interface 26 are similar to the specific configurations and the functions of the input interface 21 of the first terminal apparatus 10. The specific configuration and the functions of the data store 27 are similar to the specific configuration and the functions of the data store 22 of the first terminal apparatus 10. The data store 27 stores, for example, any information that is used for operation of the second terminal apparatus 12.

The specific configuration of the controller 28 is similar to the configuration of the controller 23 of the first terminal apparatus 10. The controller 28 controls the entire operation of the second terminal apparatus 12.

When the input interface 26 detects a user input for requesting registration as a subject to the information processing apparatus 14, the controller 28 controls the output interface 25 to output a request for input of subject information such as name, sex, age, and height of the subject. When the input interface 26 detects user input of the subject information, the controller 28 controls the communication interface 24 to send the subject information to the information processing apparatus 14. The controller 28 may send the subject information directly to the information processing apparatus 14 or indirectly by the first terminal apparatus 10 establishing short-distance wireless communication with the information processing apparatus 14. When the identification information for the subject, sent by the information processing apparatus 14 in response to sending of the subject information, is received, the controller 28 stores the identification information in the data store 27.

When the input interface 26 detects a user input for requesting specification or change of a disclosure level of the biological information record for a subject, the controller 28 controls the output interface 25 to output a request for specifying a disclosure level. The disclosure level indicates, for example, graded degrees to which a subject permits disclosure of the biological information of the subject stored in the information processing apparatus 14. The disclosure level includes, for example, "non-disclosure" that prohibits disclosure to people other than the subject and "disclosure" that allows disclosure to people other than the subject. The "disclosure" may include "personally identifiable disclosure" that allows disclosure of the record in association with information identifying the subject and "partial disclosure" that allows disclosure of the record without information identifying the subject. The information identifying the subject may be subject information or identification information for the subject. When the input interface 26 detects a user input for selecting a disclosure level, the controller 28 controls the communication interface 24 to send the disclosure level together with identification information for the subject to the information processing apparatus 14.

When a health condition of a subject is received from at least one of the first terminal apparatus 10 and the information processing apparatus 14, the controller 28 stores the health condition in the data store 27. It should be noted that, as used herein, "receive" denotes receiving information on a target, such as a health condition. When the input interface 26 detects a user input for requesting output of the health condition of the subject, the controller 28 controls the output interface 25 to output the health condition.

When response information including information for retrieving a health condition is received from the first terminal apparatus 10, the controller 28 stores the information for retrieving the health condition in the data store 27. When the input interface 26 detects a user input for requesting output of the health condition of the subject, the controller 28 controls the communication interface 24 to send to the information processing apparatus 14 a request to obtain the health condition, using the information for retrieving the health condition. When the health condition sent by the information processing apparatus 14 is received in response to the information for retrieving the health condition, the controller 28 performs control to output the health condition, using the output interface 25.

The third terminal apparatus 13 includes a communication interface 29, an output interface 30, an input interface 31, a data store 32, and a controller 33.

The communication interface 29 may include a communication module that establishes connection with the network 16. In the present embodiment, the third terminal apparatus 13 is connected to the network 16 via the communication interface 29 and communicates information The specific configuration and the functions of the output interface 30 are similar to the specific configuration and the functions of the output interface 20 of the first terminal apparatus 10. The specific configuration and the functions of the input interface 31 are similar to the specific configuration and the functions of the input interface 21 of the first terminal apparatus 10. The specific configuration and the functions of the data store 32 are similar to the specific configuration and the functions of the data store 22 of the first terminal apparatus 10. The data store 32 stores, for example, any information that is used for operation of the third terminal apparatus 13.

The specific configuration of the controller 33 is similar to the configuration of the controller 23 of the first terminal apparatus 10. The controller 33 controls the entire operation of the third terminal apparatus 13.

When information indicating the medical care history of a patient is obtained, the controller 33 stores in the data store 32 the information indicating the medical care history in association with a time at which the medical care history was obtained. The medical care history includes at least one of a diagnostic history and a treatment history. The diagnostic history includes a diagnostic result obtained in a medical examination, a health checkup, or the like. The treatment history includes details of medical treatments administered based on examinations. The controller 33 obtains the information indicating the medical care history, for example, by at least one of a user input to the input interface 31 and reception from an examination device via the communication interface 29.

When identification information for the patient is obtained, the controller 33 stores the identification information in association with data indicating the medical care history in the data store 32. The controller 33 can obtain identification information for a patient in the same manner as that of the controller 23 of the first terminal apparatus 10 for obtaining identification information for a subject. The controller 33 controls the communication interface 29 to send the information indicating the medical care history associated with the identification information and the acquisition time to the information processing apparatus 14.

The information processing apparatus 14 includes a communication interface 34, an output interface 35, an input interface 36, a data store 37, and a controller 38.

The specific configuration of the communication interface 34 is similar to the configuration of the communication interface 29 of the third terminal apparatus 13. In the present embodiment, the information processing apparatus 14 is connected to the network 16 via the communication interface 34. The functions of the communication interface 34 are similar to the functions of the communication interface 29 of the third terminal apparatus 13. For example, when the communication interface 34 sends information through the network 16, the communication interface 34 may add identification information for the information processing apparatus 14 to the information. The identification information for the information processing apparatus 14 is information that can be used to uniquely identify the information processing apparatus 14 in the information processing system 11.

The specific configuration and the functions of the output interface 35 are similar to the specific configuration and the functions of the output interface 20 of the first terminal apparatus 10. The specific configuration and the functions of the input interface 36 are similar to the specific configuration and the functions of the input interface 21 of the first terminal apparatus 10.

The specific configuration and the functions of the data store 37 are similar to the specific configuration and the functions of the data store 22 of the first terminal apparatus 10. The data store 37 stores, for example, any information that is used for operation of the information processing apparatus 14. The data store 37 stores, for example, the biological information database. The database contains biological information records of individual subjects. It should be noted that, as used herein, "contain" denotes containing information on a target such as a record. More specifically, the database is constituted by biological information for different detection times associated with identification information for a plurality of subjects. The database may contain information indicating the medical care history associated with identification information for at least one subject in a plurality of subjects.

The specific configuration of the controller 38 is similar to the configuration of the controller 23 of the first terminal apparatus 10. The controller 38 controls the entire operation of the information processing apparatus 14.

When subject information is received directly or indirectly from the second terminal apparatus 12, the controller 38 includes the subject information in the biological information database stored in the data store 37. The controller 38 generates identification information on the subject for the subject information. The controller 38 associates the generated identification information with the subject information stored in the data store 37. The controller 38 controls the communication interface 34 to send the identification information for the subject to the second terminal apparatus 12 having sent the subject information.

When a disclosure level is received directly or indirectly from the second terminal apparatus 12, the controller 38 searches the data store 37 for identification information that is the same as the identification information for the subject associated with the disclosure level. The controller 38 includes the disclosure level in the biological information database in association with the searched identification information.

When biological information on a subject associated with identification information for the subject and a detection time indicating when the biological information was detected is received from the first terminal apparatus 10, the controller 38 updates the biological information database stored in the data store 37. More specifically, the controller 38 updates a particular record associated with the received identification information for a subject in the database based on the biological information and the received detection time.

Whenever biological information on a subject is received, the controller 38 add points to reward points associated with identification information for the subject in the biological information database, in accordance with the disclosure level. By using the reward points, the subject can enjoy medical services or discounts on medical services in accordance with the number of points. The points are added, for example, as follows: no points for the disclosure level "non-disclosure"; one point for the disclosure level "partial disclosure"; and two points for the disclosure level "personally identifiable disclosure".

When the identification information for the subject stored in the second terminal apparatus 12 and the biometric authentication information are received from the first terminal apparatus 10, the controller 38 sends the biometric authentication information to the second terminal apparatus 12 and includes the biometric authentication information in the biological information database in association with the identification information for the subject in the biological information database.

When biological information on a subject is received from the first terminal apparatus 10 in association with identification information for the subject and a detection time indicating when the biological information was detected, the controller 38 retrieves a record associated with the identification information from the biological information database. It should be noted that, as used herein, "retrieve" denotes retrieving information on a target such as a record.

The controller 38 can determine the health condition of the subject based on the received biological information and the retrieved record by applying determination criteria. The determination criteria include, for example, a calculation formula in which biological information included in a biological information record is an explanatory variable and a quantified health condition is a target variable. The determination criteria are designed by researchers and the like, in advance, and input by a user to the input interface 36, or generated by the controller 38 and stored in the data store 37 as described later. It should be noted that, as used herein, "store" denotes storing information on a target such as determination criteria. The controller 38 may use information indicating a medical care history described later to determine a health condition. The controller 38 may use the season in which biological information is received to determine a health condition. The controller 38 includes the determined health condition of the subject in the biological information database in association with identification information for the subject.

Furthermore, the controller 38 sends response information based on the received biological information and the retrieved record to the first terminal apparatus 10 which sent the biological information or the second terminal apparatus 12 associated with the identification information for the subject.

As described above, the response information may include the received biological information and the retrieved biological information record, in other words, the updated biological information record. Alternatively, the response information may include the health condition of the subject which was determined by the controller 38. Alternatively, the response information may include identification information for the information processing apparatus 14 used when the second terminal apparatus 12 connects to the information processing apparatus 14 and information for identifying a health condition of a particular subject associated with the received biological information from among the health conditions of a plurality of subjects stored in the data store 37.

When information indicating a medical care history is received from the third terminal apparatus 13, the controller 38 updates the biological information database stored in the data store 37. More specifically, the controller 38 includes the information indicating the medical care history in the biological information database in association with identification information in the biological information database that is the same as the identification information for the subject received together with the information indicating the medical care history.

The controller 38 generates the determination criteria described above by using a plurality of sets, each of which is associated with respective identification information from among a plurality of subjects in the biological information database. The plurality of sets each include a biological information record and information indicating a medical care history for the same subject. The controller 38 generates the determination criteria by performing, for example, machine learning or regression analysis. It should be noted that, as used herein, "generate" denotes generating information on a target such as determination criteria. The controller 38 stores the generated determination criteria in the data store 37. In a case in which determination criteria are already stored in the data store 37, the controller 38 may update the determination criteria by using the generated determination criteria or separately store the generated determination criteria together with a generation time. The controller 38 may control the communication interface 34 to send the generated determination criteria to at least one of the first terminal apparatus 10 and the second terminal apparatus 12.

When the input interface 36 detects a user input for requesting output of records and information indicating medical care histories of a plurality of subjects, without including information identifying the subjects, the controller 38 controls the communication interface 34 to send first information described later without associating the first information with information identifying the subjects. The first information includes a record and information indicating a medical care history of particular subjects other than subjects who select "non-disclosure" as the disclosure level; in other words, particular subjects who select "disclosure" as the disclosure level in the biological information database. The controller 38 may send the first information to an information processing apparatus or the like of, for example, a research institute or an insurance company.

When the input interface 36 detects a user input for requesting output of a record for a subject with information identifying the subject, the controller 38 controls the communication interface 34 to send second information described later in association with the information identifying the subject. The second information includes a record for a particular subject who selects "personally identifiable disclosure" as the disclosure level in the biological information database. The controller 38 may control the communication interface 34 to send information indicating a medical care history together with a record. The controller 38 may send the second information to an information processing apparatus or the like of, for example, an insurance company.

Figure 2:
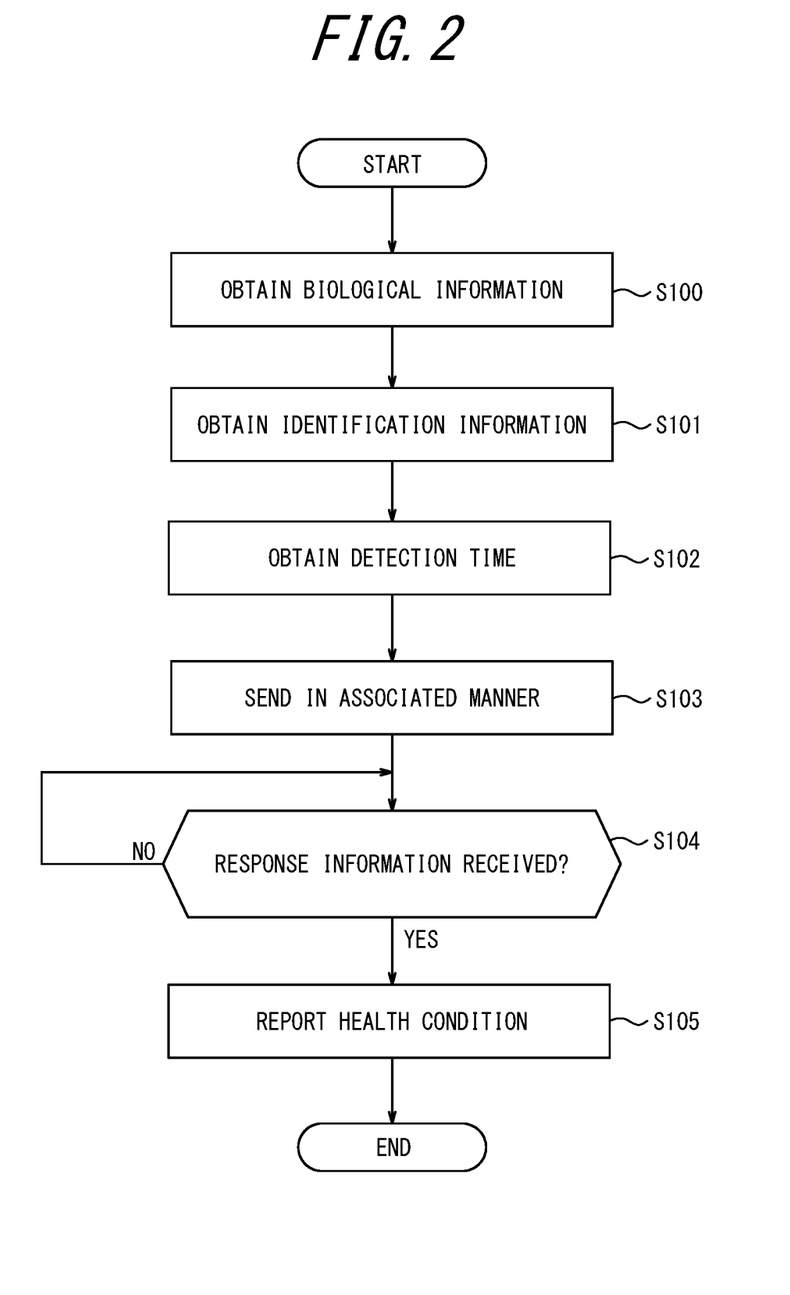
FIG. 2 is a flowchart showing biological information transmission processing performed by a controller of the first terminal apparatus in FIG. 1.

Next, biological information transmission processing performed by the controller 23 of the first terminal apparatus 10 in the present embodiment will be described with reference to the flowchart of FIG. 2. The biological information transmission processing is started when, for example, the input interface 21 detects a user input for requesting detection of biological information.

In step S100, the controller 23 controls the first sensor 17 to detect biological information. After biological information detected by the first sensor 17 is obtained, the process proceeds to step S101.

In step S101, the controller 23 controls the communication interface 19 to receive identification information for a subject from the second terminal apparatus 12 or controls the second sensor 18 to detect identification information for the subject. After the identification information is obtained by reception or detection, the process proceeds to step S102.

In step S102, the controller 23 controls the communication interface 19 or the timer to obtain a detection time indicating when the biological information was detected in step S100. After the detection time is obtained, the process proceeds to step S103.

In step S103, the controller 23 controls the communication interface 19 to send to the information processing apparatus 14 the biological information, the identification information, and the detection time obtained in steps S100, S101, and S102, respectively in an associated manner. After sending, the process proceeds to step S104.

In step S104, the controller 23 determines whether response information has been received from the information processing apparatus 14 in response to the biological information sent in step S103. In a case in which response information has not been received, the process returns to step S104 and waits. In a case in which response information has been received, the process proceeds to step S105.

In step S105, the controller 23 notifies the subject of a health condition based on the response information determined in step S104 to have been received. After notifying, the biological information transmission processing is ended.

Figure 3:
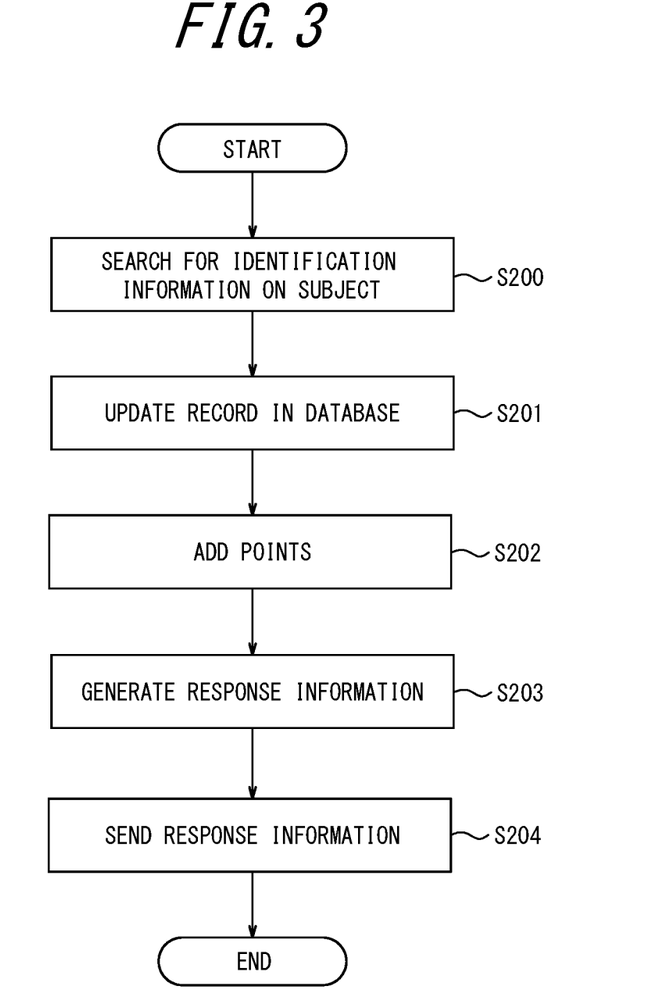
FIG. 3 is a flowchart showing biological information reception processing performed by a controller of an information processing apparatus in FIG. 1.

Next, biological information reception processing performed by the controller 38 of the information processing apparatus 14 in the present embodiment will be described with reference to the flowchart of FIG. 3. The biological information reception processing is started when, for example, biological information is received from the first terminal apparatus 10.

In step S200, the controller 38 searches the biological information database for identification information for a subject received in association with the biological information. After searching, the process proceeds to step S201.

In step S201, the controller 38 updates a biological information record associated with the identification information searched in step S200 in the database, based on a detection time received in association with the biological information. After updating, the process proceeds to step S202.

In step S202, the controller 38 adds one or more points corresponding to the disclosure level to the reward points associated with the identification information searched in step S200 in the biological information database. After addition, the process proceeds to step S203.

In step S203, the controller 38 generates response information based on the record in the biological information database updated in step S201. After generation, the process proceeds to step S204.

In step S204, the controller 38 controls the communication interface 34 to send the response information generated in step S203 to at least one of the first terminal apparatus 10 and the second terminal apparatus 12. After sending, the biological information reception processing is ended.

Figure 4:
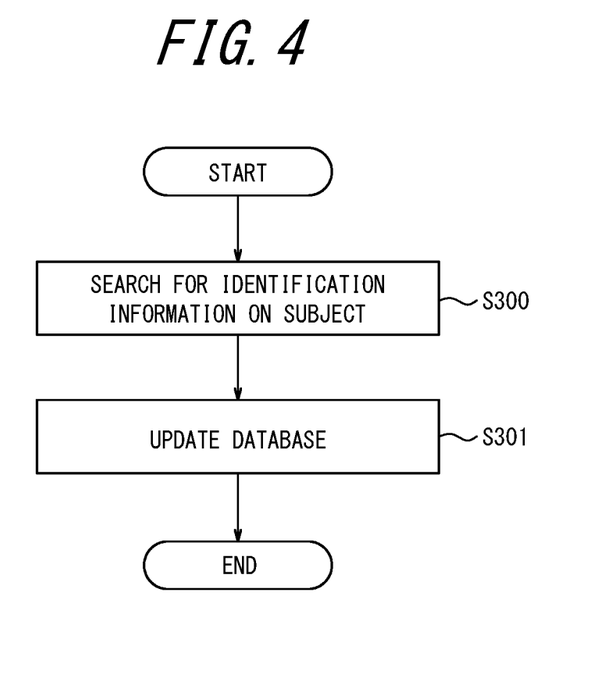
FIG. 4 is a flowchart showing medical care history reception processing performed by the controller of the information processing apparatus in FIG. 1.

Next, medical care history reception processing performed by the controller 38 of the information processing apparatus 14 in the present embodiment will be described with reference to the flowchart of FIG. 4. The medical care history reception processing is started when, for example, information indicating a medical care history is received from the third terminal apparatus 13.

In step S300, the controller 38 searches the biological information database for identification information for a subject received in association with the information indicating the medical care history. After searching, the process proceeds to step S301.

In step S301, the controller 38 updates the biological information database by adding the received information indicating the medical care history in association with the identification information searched in the biological information database in step S300. After updating, the medical care history reception processing is ended.

Figure 5:
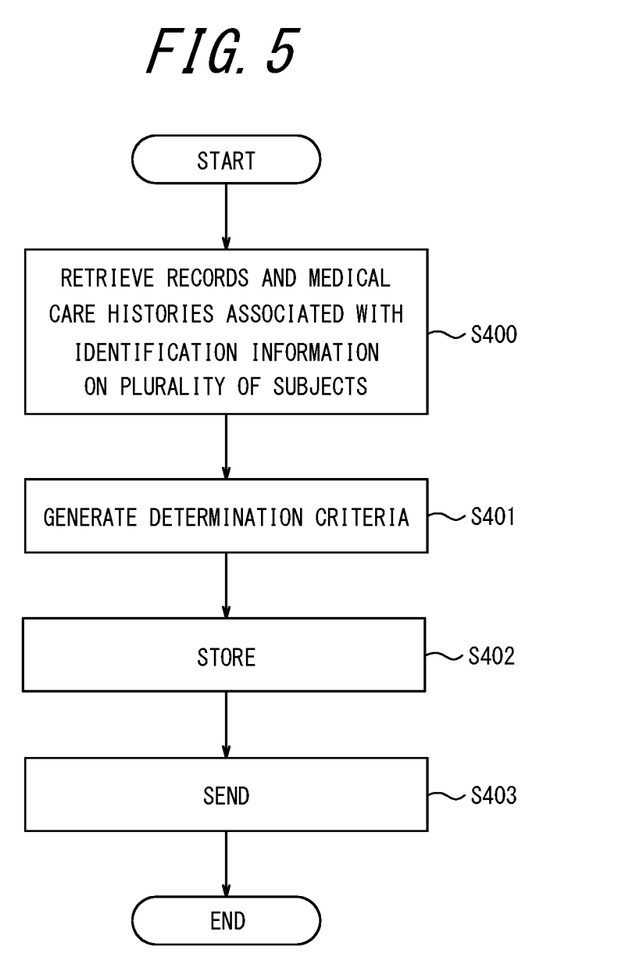
FIG. 5 is a flowchart showing determination criteria generation processing performed by the controller of the information processing apparatus in FIG. 1.

Next, determination criteria generation processing performed by the controller 38 of the information processing apparatus 14 in the present embodiment will be described with reference to the flowchart of FIG. 5. The determination criteria generation processing, for example, starts regularly, cyclically, and/or at a time at which the input interface 36 detects a user input for requesting generation of determination criteria.

In step S400, the controller 38 retrieves records and information indicating the medical care histories associated with respective identification information for each of a plurality of subjects from the biological information database. After retrieval, the process proceeds to step S401.

In step S401, the controller 38 generates the determination criteria based on the records and information indicating the medical care histories retrieved in step S400. After generation, the process proceeds to step S402.

In step S402, the controller 38 stores in the data store 37 the determination criteria generated in step S401. After storing, the process proceeds to step S403.

In step S403, the controller 38 controls the communication interface 34 to send the determination criteria stored in step S402 to at least one of the first terminal apparatus 10 and the second terminal apparatus 12. After sending, the determination criteria generation processing is ended.

Figure 6:
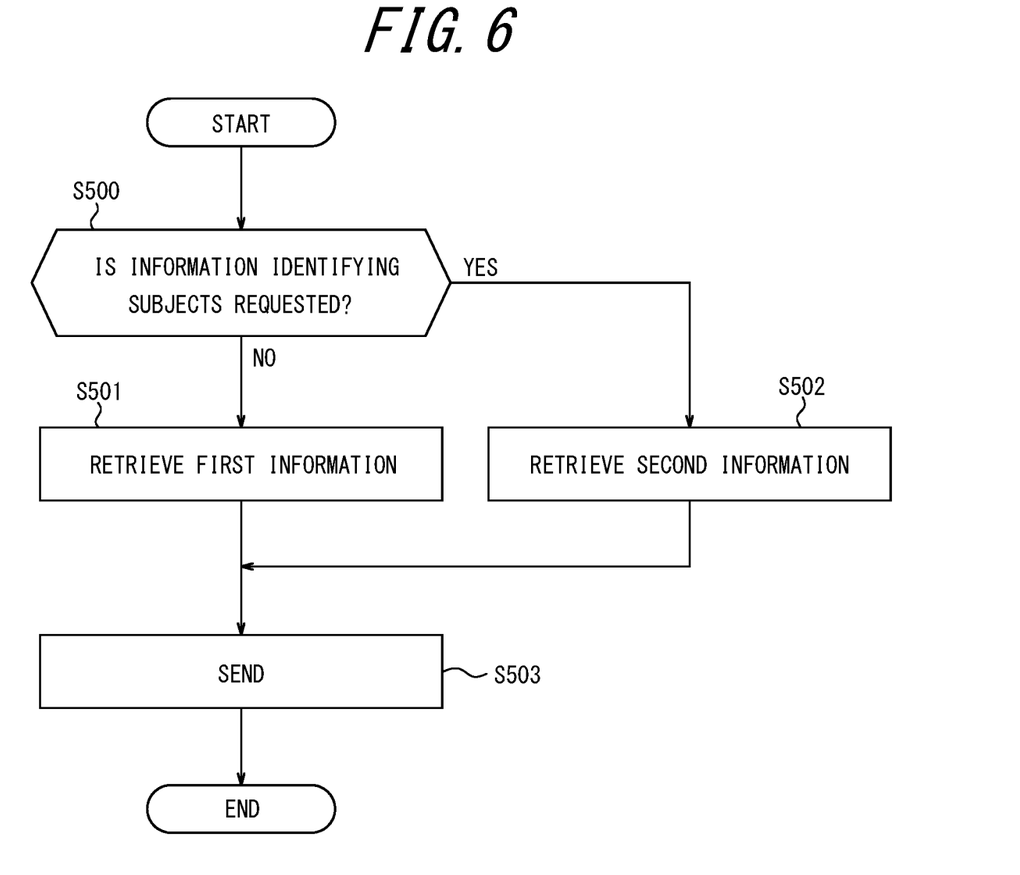
FIG. 6 is a flowchart showing record transmission processing performed by the controller of the information processing apparatus in FIG. 1.

Next, record transmission processing performed by the controller 38 of the information processing apparatus 14 in the present embodiment will be described with reference to the flowchart of FIG. 6. The record transmission processing is started when, for example, the input interface 36 detects a user input for requesting output of records of subjects.

In step S500, the controller 38 determines whether inclusion of information identifying subjects is requested in the detected user input. In a case in which inclusion of information identifying the subjects is not requested, the process proceeds to step S501. In a case in which inclusion of information identifying the subjects is requested, the process proceeds to step S502.

In step S501, the controller 38 retrieves, as the first information, one or a plurality of sets of records and information indicating medical care histories for subjects for which the disclosure level is "disclosure" from the data store 37. After retrieval, the process proceeds to step S503.

In step S502, the controller 38 retrieves, as the second information, one or a plurality of records of subjects for which the disclosure level is "personally identifiable disclosure" from the data store 37. After retrieval, the process proceeds to step S503.

In step S503, the controller 38 sends the first information or the second information retrieved in step S501 or S502, respectively, to the information processing apparatus which sent the user input detected by the input interface 36. After sending, the record transmission processing is ended.

The program configured as described above according to the present embodiment causes the first terminal apparatus 10 to execute a process including sending biological information for a subject obtained from the first sensor 17 provided in the mobile object 15 to the information processing apparatus 14 in association with identification information for the subject and a detection time. With this configuration, the program according to the present embodiment causes a computer such as the first terminal apparatus 10 to execute the process and, as a result, biological information can be collected from individual subjects who board one kind or various kinds of the mobile object 15, including public transportation. The one kind or the various kinds of the mobile object 15 will be boarded by subjects during daily life, including times with injury or illness. Therefore, the program according to the present embodiment enables collection of biological information records of subjects that are not limited to sick or injured patients; that is, biological information on subjects at multiple time points.

Furthermore, the program according to the present embodiment also causes the first terminal apparatus 10 to report a health condition of the subject based on response information sent by the information processing apparatus 14 in response to the sent biological information. With this configuration, the program according to the present embodiment can motivate people who desire to know their health condition to provide biological information. As a result, the program according to the present embodiment can promote collection of biological information from many subjects.

Moreover, in the program according to the present embodiment, the reporting of health conditions is performed by outputting the health condition using the output interface 20. With this configuration, the program according to the present embodiment enables reporting of a health condition to a subject who does not have the second terminal apparatus 12 which is for portable use in the mobile object 15.

Further, in the program according to the present embodiment, the first terminal apparatus 10 is controlled to send either the response information or the health condition to the second terminal apparatus 12 which is for portable use. With this configuration, the program according to the present embodiment enables reporting of a health condition to a subject also after the subject leaves the mobile object 15.

Furthermore, in the program according to the present embodiment, identification information for a subject is at least one of biometric authentication information obtained from the second sensor 18 and identification information obtained from the second terminal apparatus 12 which is for portable use. With this configuration, in the program according to the present embodiment, in a case in which biometric authentication information can be obtained from the second sensor 18, identification information for a subject can be obtained by the first terminal apparatus 10 without causing the subject to carry out any operation. Moreover, in the program according to the present embodiment, in a case in which identification information can be obtained from the second terminal apparatus 12, identification information for a subject can be obtained by the first terminal apparatus 10 without providing the second sensor 18.

Further, when biological information on a subject is received in association with identification information for the subject and a detection time, the information processing apparatus 14 according to the present embodiment retrieves a biological information record for the subject associated with the identification information from a biological information database and sends response information based on the received biological information on the subject and the biological information record. With this configuration, the information processing apparatus 14 can provide response information, which is the basis for generating a health condition, to the first terminal apparatus 10 or the second terminal apparatus 12 that can output the health condition.

Furthermore, when biological information on a subject is received in association with identification information for the subject and a detection time, the information processing apparatus 14 according to the present embodiment updates, in the biological information database, a biological information record for the subject associated with the identification information by using the biological information on the subject and the detection time. With this configuration, the information processing apparatus 14 can collect biological information while creating long-term records of individual subjects.

Moreover, in the information processing apparatus 14 according to the present embodiment, the biological information database contains biological information records for a plurality of subjects. When information indicating a medical care history associated with identification information for a particular subject in the plurality of subjects is received, the information processing apparatus 14 includes the information indicating the medical care history in the biological information database in association with the identification information for the particular subject. With this configuration, the information processing apparatus 14 can collect biological information records and information indicating the medical care histories for a plurality of subjects in an associated manner with respect to individual subjects and, as a result, it is possible to improve accuracy when analyzing the causal relationship between changes in biological information and diseases, and the like.

Further, the information processing apparatus 14 according to the present embodiment generates determination criteria for determining the health condition of the subject based on biological information records by using a plurality of sets which comprise a biological information record and information indicating the medical care history. The plurality of sets are associated with respective identification information for the plurality of subjects in the biological information database. With this configuration, the information processing apparatus 14 can improve accuracy when determining a health condition of a subject.

Furthermore, the information processing apparatus 14 according to the present embodiment sends a record and the like in association with or without information identifying a subject, in accordance with the disclosure level of the record. With this configuration, the information processing apparatus 14 can provide information beneficial for research and commercial use while personally identifiable information is protected based on the wishes of the subject.

While the present disclosure has been described with reference to the accompanying drawings and the examples, it should be noted that various modifications and revisions may be implemented by those skilled in the art based on the present disclosure. Accordingly, such modifications and revisions are included within the scope of the present disclosure. For example, the functions and the like included in the constituents and steps may be rearranged in a logically consistent manner; a plurality of constituents or steps may be combined together or divided.

For example, part of the processing operation performed by the first terminal apparatus 10, the second terminal apparatus 12, the third terminal apparatus 13, or the information processing apparatus 14 in the embodiment described above may be carried out by another apparatus.

Furthermore, for example, a general electronic device such as a smartphone or a computer may be configured to function as the first terminal apparatus 10, the second terminal apparatus 12, the third terminal apparatus 13, or the information processing apparatus 14 according to the embodiment described above. Specifically, a program, in which details of processing for implementing the functions of, for example, the first terminal apparatus 10 according to the embodiment are written, is stored in a memory of an electronic device, and a processor of the electronic device reads and runs the program. Thus, the disclosure according to the present embodiment may be implemented as a program that can be run by a processor. The program may be downloaded via the network 16; or the program may be stored in a portable non-transitory recording/storage medium readable by electronic devices and the program may be read from the medium by an electronic device.

Further, for example, while in the embodiment described above the first terminal apparatus 10 is installed in the mobile object 15, the same effects as those of the embodiment can also be achieved by a terminal apparatus carried by a subject or the like, such as the second terminal apparatus 12 communicating with the first sensor 17 and the second sensor 18 and performing the same operation as that of the first terminal apparatus 10 in the embodiment.

The invention claimed is:

1. An information processing system comprising:
a first terminal apparatus installed in a vehicle and configured to:
receive from a first sensor provided in the vehicle and configured to detect fluctuating biological information on a subject who boards the vehicle during daily life, the detected fluctuating biological information;
as identification information for the subject, (i) receive, from a second sensor provided in the vehicle and configured to detect biometric authentication information that is unique and constant for the subject, the detected biometric authentication information, or (ii) receive, from a second terminal apparatus carried by the subject and configured to send information that can be used to uniquely identify the subject, the sent information;
obtain a detection time indicating when the fluctuating biological information is detected by the first sensor; and
send the fluctuating biological information in association with the identification information for the subject and the detection time via a network; and
an information processing apparatus comprising:
a database configured to contain biological information records of a plurality of subjects and respective disclosure levels of the biological information records selected by the plurality of subjects in association with identification information for the plurality of subjects, the biological information records including fluctuating biological information detected by the first sensor at multiple time points; and
a controller configured to:
upon receiving the fluctuating biological information in association with the identification information for the subject and the detection time from the first terminal apparatus, update a biological information record associated with the received identification information for the subject in the database based on the received fluctuating biological information and the received detection time;
in response to a request for records without information identifying subjects, send biological information records, in the database, associated with identification information for first subjects other than subjects who have selected disclosure levels that prohibit disclosure among the plurality of subjects, in no association with information identifying the first subjects, to another information processing apparatus; and
in response to a request for records with information identifying subjects, send biological information records, in the database, associated with identification information for second subjects who have selected disclosure levels that allow disclosure in a personally identifiable manner among the plurality of subjects, in association with information identifying the second subjects, to another information processing apparatus.

2. The information processing system according to claim 1, wherein the first terminal apparatus installed in the vehicle is further configured to report a health condition of the subject based on response information sent by the information processing apparatus in response to the sent fluctuating biological information.

3. The information processing system according to claim 2, wherein
the response information includes a biological information record for the subject, and
the first terminal apparatus determines the health condition of the subject based on the biological information record.

4. The information processing system according to claim 2, wherein
the response information includes the health condition of the subject determined based on a biological information record for the subject.

5. The information processing system according to claim 2, wherein
the reporting the health condition includes outputting the health condition of the subject.

6. The information processing system according to claim 2, wherein
the reporting the health condition includes sending either the response information or the health condition to the second terminal apparatus carried by the subject.

7. The information processing system according to claim 6, wherein
the response information includes information for retrieving the health condition of the subject from the information processing apparatus storing the health condition determined based on a biological information record.

8. An information processing method implemented by a system including a first terminal apparatus installed in a vehicle and an information processing apparatus, the method comprising:
receiving, by the first terminal apparatus, from a first sensor provided in the vehicle and configured to detect fluctuating biological information on a subject who boards the vehicle during daily life, the detected fluctuating biological information;
as identification information for the subject, (i) receiving, by the first terminal apparatus, from a second sensor provided in the vehicle and configured to detect biometric authentication information that is unique and constant for the subject, the detected biometric authentication information, or (ii) receiving, by the first terminal apparatus, from a second terminal apparatus carried by the subject and configured to send information that can be used to uniquely identify the subject, the sent information;

obtaining, by the first terminal apparatus, a detection time indicating when the fluctuating biological information is detected by the first sensor;

sending, by the first terminal apparatus, the fluctuating biological information in association with the identification information for the subject and the detection time via a network;

maintaining, by the information processing apparatus, a database configured to contain biological information records of a plurality of subjects and respective disclosure levels of the biological information records selected by the plurality of subjects in association with identification information for the plurality of subjects, the biological information records including fluctuating biological information detected by the first sensor at multiple time points;

upon receiving the fluctuating biological information in association with the identification information for the subject and the detection time from the first terminal apparatus, updating, by the information processing apparatus, a biological information record associated with the received identification information for the subject in the database based on the received fluctuating biological information and the received detection time;

in response to a request for records without information identifying subjects, sending, by the information processing apparatus, biological information records, in the database, associated with identification information for first subjects other than subjects who have selected disclosure levels that prohibit disclosure among the plurality of subjects, in no association with information identifying the first subjects, to another information processing apparatus; and in response to a request for records with information identifying subjects, sending, by the information processing apparatus, biological information records, in the database, associated with identification information for second subjects who have selected disclosure levels that allow disclosure in a personally identifiable manner among the plurality of subjects, in association with information identifying the second subjects, to another information processing apparatus.

9. The information processing system according to claim 1, wherein the information processing system collects biological information on a group of people that is not limited to sick or injured patients at multiple time points.

10. The information processing system according to claim 1, wherein the vehicle is a public transportation vehicle, the first sensor is provided on a handrail of the public transportation vehicle, and the plurality of subjects include passengers of the public transportation vehicle.

11. The information processing system according to claim 1, wherein the database is further configured to store reward points in association with the identification information for the plurality of subjects, and the controller is further configured to:

upon receiving the fluctuating biological information in association with the identification information for the subject and the detection time from the first terminal apparatus, add points to the reward points associated with the received identification information for the subject in the database, in accordance with a disclosure level associated with the received identification information for the subject in the database.

* * * * *